United States Patent [19]

Klainer et al.

[11] Patent Number: 4,824,206
[45] Date of Patent: Apr. 25, 1989

[54] MODULAR FIBER OPTIC CHEMICAL SENSOR

[75] Inventors: Stanley M. Klainer, San Ramon, Calif.; J. Milton Harris, Huntsville, Ala.; Kisholoy Goswami, Walnut Creek, Calif.

[73] Assignee: ST&E, Inc., Livermore, Calif.

[21] Appl. No.: 125,259

[22] Filed: Nov. 25, 1987

[51] Int. Cl.$^4$ ............................ G02B 6/02; G02B 6/16
[52] U.S. Cl. ................................. 350/96.29; 350/96.33
[58] Field of Search ................ 350/96.29, 96.30, 96.33

[56] References Cited

U.S. PATENT DOCUMENTS

| | | | |
|---|---|---|---|
| 4,655,545 | 4/1987 | Yamanishi et al. | 350/96.29 |
| 4,682,895 | 7/1987 | Costello | 350/96.29 |
| 4,712,865 | 12/1987 | Hsu et al. | 350/96.29 |
| 4,718,747 | 1/1988 | Bianchi et al. | 350/96.29 |

Primary Examiner—William L. Sikes
Assistant Examiner—Robert E. Wise
Attorney, Agent, or Firm—Henry P. Sartorio

[57] ABSTRACT

A modular fiber optic chemical sensor (FOCS) is formed using a capillary tube clad. A fiber optic core with reactive surface is exposed to a sample environment and then the capillary tube is fitted over the core. The capillary could also be porous so that in-situ measurements can be made. The capillary can be spaced from the core so that a flow channel for gas and liquid sensing is formed, or an index matching fluid may fill the channel. Measurements can be made in a compact portable modular detector unit in which the FOCS is placed between an excitation source and a detector or single ended where the excitation source and detector are at the same end of the core and a reflector is placed at the end of the core.

20 Claims, 2 Drawing Sheets

MODULAR FIBER OPTIC CHEMICAL SENSOR

BACKGROUND OF THE INVENTION

The invention relates generally to fiber optic sensors, and more particularly to the structure, including the fiber optic clad, in a modular fiber optic sensor.

Fiber optic sensors utilize the transmission properties of an optical fiber, which is a function of the refractive indexes of the core and the clad. For good transmission of light through the fiber, the index of the clad must be lower than the index of the core. The typical fiber optic sensor places a specific chemistry reaction system at the tip of a standard fiber. The tip is exposed to the sampling environment and the fiber is used to transmit an excitation signal and/or a response signal. Sensors have been made by placing the reaction chemistry along the side of a fiber core to enhance its signal. U.S. patent application Ser. No. 046,986 filed May 6, 1987 teaches the formation of a fiber optic sensor in which the reactive material forms the clad itself, or alternatively is sandwiched between the core and the clad in cases where the reactive material is unsuitable or undesirable for the clad. In the sandwich configuration, the clad must be porous, with holes of the right size to allow the desired species to contact the reactive layer. In such cases it is difficult to form a good clad layer. In all of those configurations, the measurements are made with the sensor in-situ. It is desireable to have a simple and widely applicable method for forming a clad on a fiber optic sensor in order to provide maximum interaction between the active surface and the analyte. It is also desireable to have a modular sensor configuration which allows measurements to be made after the sensor is removed from the sampling environment.

SUMMARY OF THE INVENTION

Accordingly it is an object of the invention to provide an improved method for forming a clad for a fiber optic sensor.

It is also an objective of the invention to provide an improved clad for a fiber optic sensor.

It is also an objective to produce a modular clad for a fiber optic sensor.

It is also the objective to be able to place the clad on the core after the reaction between the active surface and analyte has occurred (and the surfaces washed or treated, if needed).

It is another object of the invention to provide a modular fiber optic chemical sensor in which the measurements can be made after the sensor is removed from the sampling environment.

The invention is an improved pull-on clad, and method for forming same on a fiber optic sensor and the resulting modular fiber optic chemical sensor. A fiber optic core is prepared for use in a sensor, including attaching the reactant species to the surface of the core. The core with reactive surface is placed in the sampling environment, then removed and further treated (if necessary). After this exposure to the sample and subsequent removal, a capillary tube of the appropriate refractive index and of the appropriate diameter to fit tightly over the core is pulled over the core (or the core is inserted into the capillary) to form the clad, sandwiching therein the reactive agent immobilized on the core surface. Measurements can now be made, e.g. in a compact tester unit, of the modular fiber optic chemical sensor by inputing an excitation signal of the appropriate wavelength and detecting a response signal from the reactive layer. The capillary tube may also have the desired porosity so the sensor can be used in-situ. In alternate configurations, the capillary tube clad is separated from the core by spacers which provide for either gas or liquid flow, or for the use of a refractive index matching fluid.

DETAILED DESCRIPTION OF THE PREFERRED EMBODIMENTS

The invention is a method of forming a fiber optic sensor, and the resulting fiber optic sensor apparatus. A capillary tube is used as the clad for a fiber optic core which has an immobilized reactive layer thereon. The core with reactive layer is exposed to the sampling environment and removed before the capillary clad is attached. The capillary tube then completes a modular configuration making the core/reactive surface into a fiber optic. In one embodiment, the capillary tube may be porous to allow the detected species to contact the reactive layer through the clad. In other embodiments the capillary tube may be spaced apart from the core by spacer elements to allow gas or liquid flow over the reactive surface, or the use of an index matching fluid.

Figure 1A:
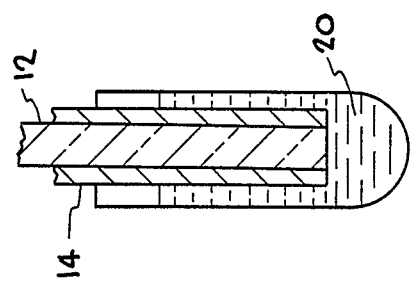
FIGS. 1 A-F illustrate the formation of a modular fiber optic chemical sensor (FOCS) having a fiber optic core with reactive surface within a capillary tube clad.
Figure 1B:
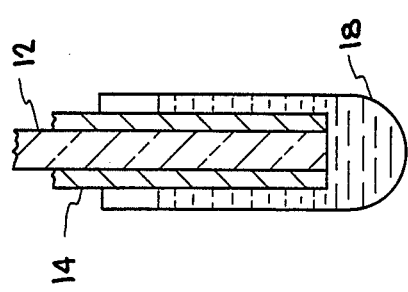
Figure 1C:
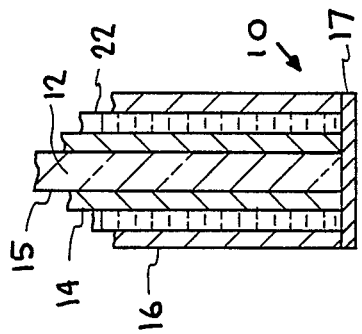
Figure 1D:
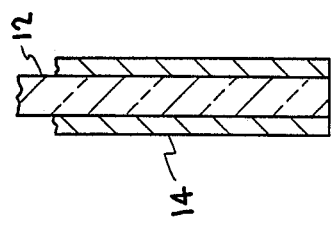
Figure 1E:
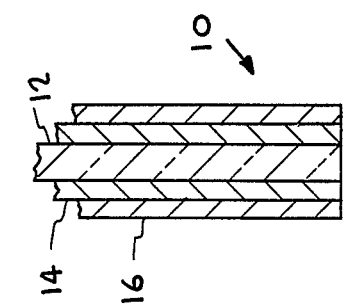

As shown in FIG. 1E, a fiber optic chemical sensor (FOCS) 10 is formed of a fiber optic core 12 of refractive index $N_1$, with a reactive layer (active surface) 14 of refractive index $N_3$ immobilized on the core 12, and surrounded be a capillary tube 16 of refractive index $N_2$ which forms the clad. By proper selection of the refractive indexes $N_1$, $N_2$, $N_3$ the sensor 10 will function as a fiber optic waveguide and transmit light therethrough to excite the reactive layer 14 and/or produce a response signal determined by the presence of the reactive species of interest. Thus the primary function of capillary tube 16 is to provide a cladding so the sensor will operate as a fiber optic to propagate light signals. Secondary functions are to provide protection for the reactive layer and to permit the species of interest to come into contact with the reactive layer, in-situ, if the capillary is perforated.

The fiber optic sensor is formed by the sequence shown in FIGS. 1A-F. A fiber optic core 12 of suitable refractive index $N_1$ and transmission properties for the operative signal wavelengths is selected. The fiber core will typically have a diameter of 100–1000 microns. An active surface 14 of refractive index $N_3$ greater than $N_1$ is formed on the core by attaching or immobilizing suitable reactants to the core surface. The reactive layer 14 can be formed with monoclonals, polyclonals, enzymes, or other organics which are specific to a particular species, or groups to be detected, and is attached by known means. The core with active surface is placed in a test solution (analyte) 18 and allowed to react. The reacted system is then washed and stabilized in a buffer solution 20. A tight fitting capillary tube 16 of suitable refractive index $N_2$ less than $N_1$ is slid over the core (or the core is inserted into the capillary tube) to form the clad and to form a protective layer over the reactive surface.

Figure 1F:
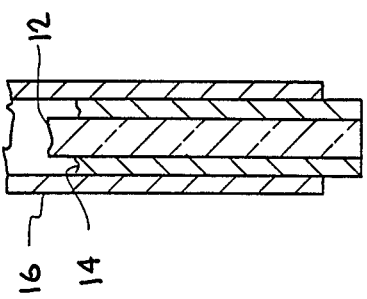

The capillary can be coated with a suitable index matching fluid 22 of refractive index $N_v$ as shown in FIG. 1F, to form a better interface and index match (and also make it easier to slide the capillary onto the core). When $N_v$ is greater than $N_1$ the index matching fluid functions primarily to form a better interface while capillary tube 16 forms the clad for the waveguide. However, in some instances available capillary tubes may not have the desired $N_2$ to form the clad. Then by choice of an index matching fluid with $N_v$ less than $N_1$, the index matching fluid is effectively the clad and the capillary tube clad (whose index $N_2$ is now irrelevant) serves primarily as a structural part of the FOCS.

The capillary can also include suitably sized pores to allow the species of interest to pass through the clad to the reactive layer so that the sensor can be used in-situ, instead of a solid capillary which seals the reactive layer after it has been exposed to the sample environment. In all cases the sensor can then be used in the standard manner for fluorescence/absorption/refraction measurements. Excitation light can be transmitted through the fiber to the reactive layer and light generated by the reactive layer can be transmitted out of the fiber. A closed capillary with either a reflective or nonreflective end 17 can be used or an open capillary can be used. The use of a reflective porous capillary provides a design for single-ended, in-situ measurements. The fiber optic sensor will be used in combination with suitable excitation means and detection means.

Figure 2:
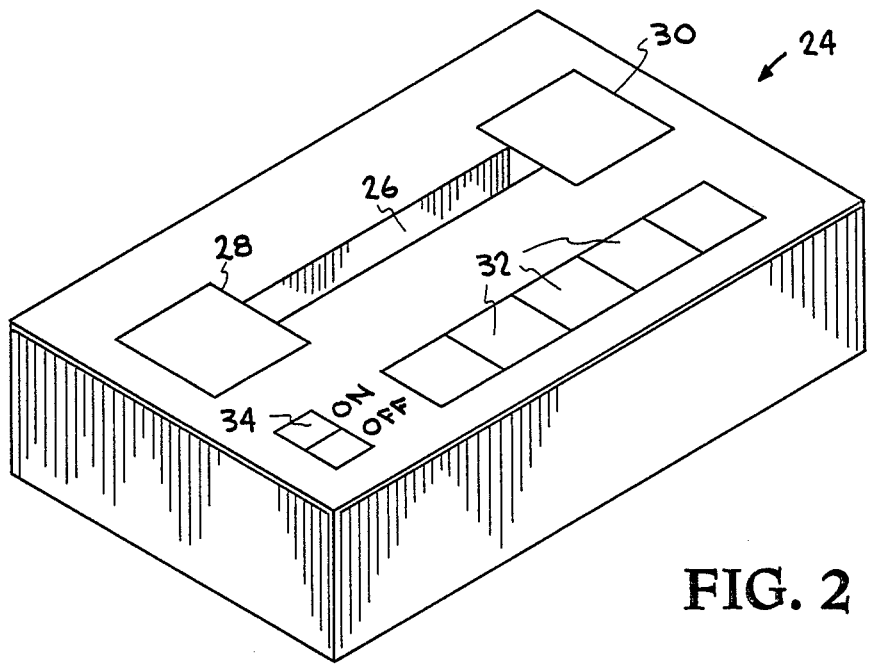
FIG. 2 shows a compact portable modular detector.

In one preferred embodiment, the FOCS of the invention is used in combination with a compact portable modular detector unit, as shown in FIG. 2. The detector unit 24 has a channel 26 extending between a source 28 and detector 30. A FOCS of a predetermined length fits into channel 26 and butts up against source 28 and detector 30 so that measurements can be made. The results are shown on display 32. The unit 24 is activated by on/off switch 34, and is powered by conventional means, e.g. batteries. Source 28 and detector 30 are conventional components, e.g. a laser diode and diode detector. The unit is extremely compact. Different FOCS can be placed into the unit. Other connection methods can also be used.

Figures 3A, 3B:
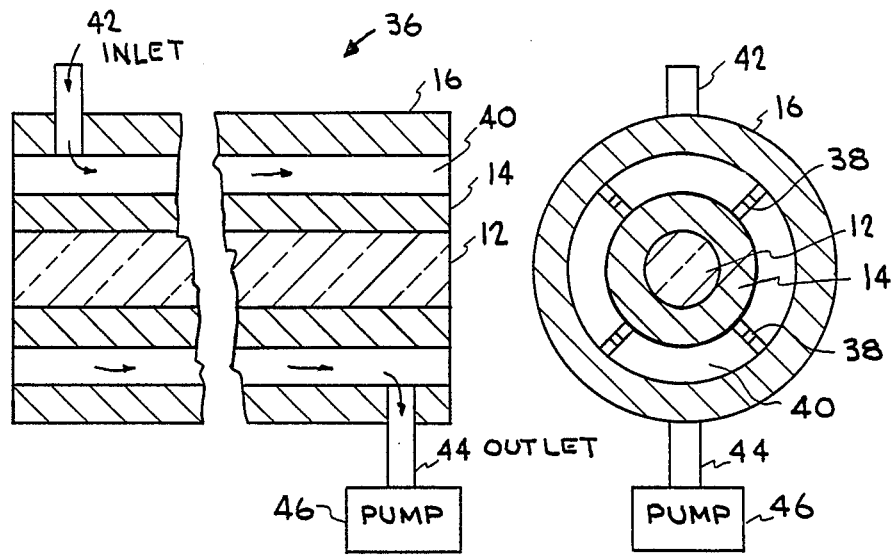
FIGS. 3A, B show a flow-through modular FOCS.

In an alternate embodiment of the invention, as shown in FIGS. 3A, B, a sensor 36 has a capillary 16 which is spaced apart from the core 12 with its reactive surface 14 by means of spacers 38 which provide an annular flow channel 40 between the core and clad. An inlet 42 and outlet 44 are provided to flow channel 40. A pump 44 can be used to pull a gas or a liquid through the annular flow channel 40 over the reactive surface 14. In this case capillary clad 16 is not porous. Sensor 36 is then a gas or liquid sensor. The spacers 38 may be annular disks with a plurality of gas permeable holes (which may filter out particulates) to permit gas flow, or a plurality of struts for liquid flow as shown in FIG. 3B or other suitable spacing means. The spacers 38 can be optically transparent so they will not effect light transmission. If the spacing between the reactive surface and the capillary is small, the refractive index of the gas or liquid is not a consideration. For larger spacing, the index of refraction of the flowing gas or liquid must be greater than the core.

In a further embodiment of the invention, a grating 15 is put on the core by etching, polymers or other suitable means before the immobilization of the reactive surface is done to enhance sensitivity. This should allow the use of active surfaces of monolayers, and will control the monochromaticity of exciting light.

Changes and modifications in the specifically described embodiments can be carried out without departing from the scope of the invention which is intended to be limited only by the scope of the appended claims.

We claim:

1. A fiber optic sensor comprising:
   a fiber core;
   a reactive surface formed on the core;
   a capillary tube disposed about the core and reactive surface to form a fiber optic clad and a protective layer for the reactive surface.

2. The sensor of claim 1 wherein the capillary tube is spaced apart from the core and reactive surface to form a flow channel to permit gas and liquid flow between the tube and core over the reactive layer.

3. The sensor of claim 2 further comprising spacing means for maintaining the tube in a spaced relationship with the core and refractive surface to form the flow channel, and inlet and outlet means communicating with the flow channel for flowing gas and liquid through the flow channel.

4. The sensor of claim 1 wherein the capillary tube is fitted over the core after the reactive surface has been exposed to a sample environment.

5. The sensor of claim 1 wherein the capillary tube is porous, with pore size to enable a predetermined species to contact the reactive surface through the capillary tube.

6. The sensor of claim 1 wherein the fiber core has a refractive index $N_1$, the reactive surface has a refractive index $N_3$, and the capillary tube clad has a refractive index $N_2$, where $N_2 < N_1 < N_3$.

7. The sensor of claim 1 further comprising an index matching fluid between the capillary tube and the reactive surface.

8. The sensor of claim 7 wherein the index matching fluid has a refractive index $N_v$ less than the core and fills an annular channel between the reactive surface and capillary tube to form an effective clad for the sensor.

9. The sensor of claim 7 wherein the index matching fluid has a refractive index $N_v$ greater than the core and the capillary tube has a refractive index less than the core.

10. The sensor of claim 1 further including excitation means and detection means operatively associated with the fiber optic sensor.

11. The sensor of claim 10 wherein the fiber optic sensor, excitation means, and detection means are mounted in a compact portable detection unit.

12. The sensor of claim 1 wherein the core has a grating formed thereon.

13. The sensor of claim 1 wherein the capillary tube has a reflective closed end.

14. A method of forming a fiber optic sensor, comprising:
    forming a reactive surface on a fiber optic core;
    enclosing the fiber optic core with reactive surface in a capillary tube to form a fiber optic clad.

15. The method of claim 14 further comprising:
    exposing the fiber optic core with reactive surface to a sample environment prior to enclosing in a capillary tube.

16. The method of claim 15 further comprising:

treating the exposed fiber optic core with reactive surface to stabilize the surface prior to enclosing in a capillary tube.

17. The method of claim 14 further comprising:
forming the capillary tube of a porous capillary tube with a pore size that transmits a predetermined species to contact the reactive surface.

18. The method of claim 14 further comprising spacing the capillary tube apart from the core with reactive surface to form a flow channel for gases and liquids.

19. The method of claim 14 further comprising placing an index matching fluid between the capillary tube and reactive layer.

20. The method of claim 19 further comprising forming the index matching fluid with a refractive index less than the core.

* * * * *